United States Patent
Kajiki et al.

(10) Patent No.: US 11,225,623 B2
(45) Date of Patent: Jan. 18, 2022

(54) ESTER FOR REFRIGERATOR OILS

(71) Applicant: NOF CORPORATION, Tokyo (JP)

(72) Inventors: Takeshi Kajiki, Amagasaki (JP); Fumitaka Yoshikawa, Nishinomiya (JP); Seita Ueda, Nishinomiya (JP)

(73) Assignee: NOF CORPORATION, Tokyo (JP)

( * ) Notice: Subject to any disclaimer, the term of this patent is extended or adjusted under 35 U.S.C. 154(b) by 833 days.

(21) Appl. No.: 16/065,253

(22) PCT Filed: Dec. 19, 2016

(86) PCT No.: PCT/JP2016/087713
§ 371 (c)(1),
(2) Date: Jun. 22, 2018

(87) PCT Pub. No.: WO2017/110711
PCT Pub. Date: Jun. 29, 2017

(65) Prior Publication Data
US 2021/0207050 A1  Jul. 8, 2021

(51) Int. Cl.
| | | |
|---|---|---|
| *C10M 105/38* | (2006.01) | |
| *C09K 5/04* | (2006.01) | |
| *C10N 20/02* | (2006.01) | |
| *C10N 40/30* | (2006.01) | |

(52) U.S. Cl.
CPC .......... *C10M 105/38* (2013.01); *C09K 5/045* (2013.01); *C09K 2205/122* (2013.01); *C09K 2205/24* (2013.01); *C10M 2207/2835* (2013.01); *C10N 2020/02* (2013.01); *C10N 2040/30* (2013.01)

(58) Field of Classification Search
CPC ........ C10M 105/38; C10M 2207/2836; C10N 2020/02; C10N 2040/30; C09K 5/045; C09K 2205/24; C09K 2205/122
See application file for complete search history.

(56) References Cited

U.S. PATENT DOCUMENTS

| | | | | |
|---|---|---|---|---|
| 5,833,876 A * | 11/1998 | Schnur | ............ | C10M 129/72 252/68 |
| 5,906,769 A | 5/1999 | Schnur et al. | | |
| 7,176,169 B2 * | 2/2007 | Gibb | ............ | C10M 171/008 508/485 |
| 8,318,647 B2 * | 11/2012 | Carr | ............ | C10M 107/32 508/485 |
| 8,772,530 B2 | 7/2014 | Inayama et al. | | |
| 9,005,470 B2 | 4/2015 | Takigawa et al. | | |
| 2010/0181523 A1 * | 7/2010 | Kelley | ............ | C10M 105/38 252/67 |
| 2013/0207022 A1 | 8/2013 | Hessell et al. | | |
| 2013/0207023 A1 | 8/2013 | Benanti et al. | | |
| 2016/0281017 A1 | 9/2016 | Tsaih et al. | | |

FOREIGN PATENT DOCUMENTS

| | | | |
|---|---|---|---|
| JP | 2015-140352 A | | 8/2015 |
| JP | 2016-148011 A | | 8/2016 |
| JP | 2016-188356 A | | 11/2016 |
| WO | 00/75258 A1 | | 12/2000 |
| WO | 2012/026214 A1 | | 3/2012 |
| WO | 2012/026303 A1 | | 3/2012 |
| WO | 2013/046822 A1 | | 4/2013 |
| WO | 2013/123186 A1 | | 8/2013 |

OTHER PUBLICATIONS

International Search Report for PCT/JP2016/087713 dated Jan. 17, 2017 (PCT/ISA/210).
Communication dated Jul. 11, 2019 by the European Patent Office in application No. 16878600.2.

* cited by examiner

*Primary Examiner* — Cephia D Toomer
(74) *Attorney, Agent, or Firm* — Sughrue Mion, PLLC

(57) ABSTRACT

It is provided an ester for a refrigerator oil and of mixed alcohols and mixed monocarboxylic acids. The mixed alcohols include dipentaerythritol and tripentaerythritol in a mass ratio of 90/10 to 99.7/0.3, and the mixed monocarboxylic acids include n-pentanoic acid and 2-methyl butanoic acid in a mass ratio of 50/50 to 80/20. The ester has a kinematic viscosity of 50 to 150 mm$^2$/s at 40° C.

2 Claims, No Drawings

ESTER FOR REFRIGERATOR OILS

CROSS REFERENCE TO RELATED APPLICATIONS

This application is a National Stage of International Application No. PCT/JP2016/087713 filed Dec. 19, 2016, claiming priority based on Japanese Patent Application No. 2015-253706, filed Dec. 25, 2015.

TECHNICAL FIELD

The present invention relates to a carboxylic ester suitable for a lubrication oil for a refrigerator using R-32 refrigerant.

BACKGROUND ARTS

Recently, as freon refrigerant substitutes have high Global Warming Potentials, it has been studied substitute refrigerants for reducing use amounts of the Freon refrigerants. Refrigerants used for house-hold refrigerators have been shifted to hydrocarbon refrigerants, such as R-600a refrigerant, having low Global Warming Potentials. Further, as to refrigerants for room air conditioners, the substitute refrigerants has been intensively studied.

At present, various kinds of candidates are known as the substitute refrigerant of R-410A refrigerant, which is mainly used as the refrigerant for a room air conditioner. Among them, R-32 refrigerant is deemed as a main candidate, it is proceeded the development of a ester for a refrigerator oil compatible with R-32 refrigerant.

According patent document 1, as such ester, it is proposed a ester using a fatty acid having a carbon number of 7 to 9 and lactic acid or isobutyric acid belonging to an aliphatic carboxylic acid having a carbon number of 4. According to patent document 2, it is disclosed an ester for a refrigerator oil of pentaerythritol and isobutyric acid and 3, 5, 5-trimethyl hexanoic acid.

It is used rotary system and screw system for a compressor in an air conditioning system such as a room air conditioner. It is required high lubrication property for a refrigerator oil used for such compressor. As the ester for the refrigerator oil, it is necessary a kinematic viscosity of 50 mm$^2$/s or higher at 40° C. Recently, in addition to this, on the viewpoint of improving energy saving property, it is general to operate an equipment efficiently and flexibly in response to circumstances by means of inverter control system. Temperature ranges during operation at the respective positions of a refrigerator system, such as a compressor, condenser, expansion valve and evaporator, are wider than those in a prior system from a low temperature to a high temperature. As a refrigerator oil circulates in the refrigerator system with a refrigerant, it is demanded properties of having compatibility with the refrigerant in a wide temperature and concentration ranges. It is thus demanded an ester for a refrigerator oil having a high kinematic viscosity and compatibility with R-32 refrigerant.

Further, it is known that cooling performance of R-32 refrigerant is better than R-410A refrigerant due to its temperature characteristics. However, for utilizing the excellent performance, it is necessary to operate the compressor efficiently at a temperature and pressure higher than those of R-410A refrigerant. It is thus demanded higher heat-resistant property for the used ester for the refrigerator oil.

RELATED ART DOCUMENTS

Patent Documents (Patent document 1) WO 2012/026214 A1
(Patent document 2) WO 2012/026303 A1

SUMMARY OF THE INVENTION

Object to be Solved by the Invention

Therefore, an object of the present invention is to provide an ester for a refrigerator oil having high compatibility with R-32 refrigerant, high lubrication property and excellent heat resistance.

Solution for the Object

The present invention provides an ester for a refrigerator oil and of mixed alcohols and mixed monocarboxylic acids,
wherein said mixed alcohols comprise dipentaerythritol and tripentaerythritol in a mass ratio of 90/10 to 99.7/0.3;
wherein said mixed monocarboxylic acids comprise n-pentanoic acid and 2-methyl butanoic acid in a mass ratio of 50/50 to 80/20; and
wherein said ester has a kinematic viscosity of 50 to 150 mm$^2$/s at 40° C.

The present invention further provides a working fluid composition for a refrigerator, said fluid composition comprising a mixture of said ester for said refrigerator oil and R-32 refrigerant.

Effects of the Invention

According to the present invention, it is possible to provide an ester for a refrigerator oil having high compatibility with R-32 refrigerant, high lubrication property and excellent heat resistance.

EMBODIMENTS FOR CARRYING OUT THE INVENTION

The ester for the refrigerator oil used in the present invention is of an ester of mixed alcohols of dipentaerythritol and tripentaerythritol and mixed monocarboxylic acids of n-pentanoic acid and 2-methyl butanoic acid.

Provided that 100 mass percent is assigned to a total mass of dipentaerythritol and tripentaerythritol, the content of tripentaerythritol is made 0.3 mass percent or higher (preferably 0.5 mass percent or higher). It is thereby possible to obtain the ester for the refrigerator oil having high lubrication property.

Further, the content of tripentaerythritol is made 10 mass percent or lower (preferably 8 mass percent or lower). It is thereby possible to obtain the ester for the refrigerator oil having high compatibility with R-32 refrigerant and high heat resistance enduring operation at a high temperature in an equipment using R-32 refrigerant.

As to the ratio of n-pentanoic acid and 2-methyl butanoic acid used in the ester for the refrigerator oil of the present invention, on the viewpoint of solubility to R-32 refrigerant, lubrication property and heat resistance, the mass of n-pentanoic acid is preferably 50 to 80 mass percent and the mass of n-pentanoic acid is preferably 20 to 50 mass percent. However, 100 mass percent is assigned to a total mass of n-pentanoic acid and 2-methyl butanoic acid. In the case that the ratio of n-pentanoic acid is 50 mass percent or higher (more preferably 55 mass percent or higher), it is possible to obtain the ester for the refrigerator oil having high lubrication property. In the case that the ratio of n-pentanoic acid is 80 mass percent or lower (more preferably 75 mass percent or lower), it is possible to obtain the ester for the refrigerator oil excellent in heat resistant property.

The ester for the refrigerator oil of the present invention has a kinematic viscosity of 50 to 150 mm$^2$/s at 40° C. In the case that the kinematic viscosity at 40° C. is smaller than 50 mm$^2$/s, the lubrication property is insufficient. In the case that the kinematic viscosity at 40° C. is larger than 150 mm²/s, the compatibility with R-32 refrigerant is deteriorated to adversely affect the energy-saving property of the equipment.

The ratio R defined by the following formula of the ester for the refrigerator oil of the present invention may preferably be 3 or larger and more preferably be 6 or larger. Further, the following ratio R may preferably be 200 or lower and more preferably be 130 or lower. In the case that the ratio R of the compositions of the mixed alcohols and mixed carboxylic acids in the ester for the refrigerator oil is in this range, the compatibility with the R-32 refrigerant demanded by the present invention is high, so that it is possible to attain the performances of obtaining the heat resistance and lubricating property at high levels.

$$R=(\text{mass \% of 2-methyl butanoic acid/mass \% of } n\text{-pentanoic acid})/(\text{mass \% of tripentaerythritol/mass \% of dipentaerythritol}) \quad \text{Formula 1}$$

According to the present invention, it is used the ester for the refrigerator oil and of mixed alcohols of dipentaerythritol and tripentaerythritol and mixed monocarboxylic acids of n-pentanoic acid and 2-methyl butanoic acid. The ester for the refrigerator oil preferably has a hydroxyl value of 10.0 mgKOH/g or lower and an acid value of 0.1 mgKOH/g or lower. The hydroxyl value may preferably be 5.0 mgKOH/g or lower and most preferably be 1.0 mgKOH/g or lower. Further, the acid value is preferably as low as possible, preferably 0.05 mgKOH/g or lower and more preferably be 0.02 mgKOH/g or lower.

The ester for the refrigerator oil of the present invention can be produced by conventional direct esterification of the carboxylic acids and alcohols. Specifically, as to the equivalent ratio of the specific alcohols and carboxylic acids as described above, normally, an excess amount of carboxyl group of the carboxylic acids may be suitably added with respect to 1 equivalent of the alcohols, and a catalyst may be optionally added. Further, a solvent may be optionally used. The solvent used preferably has a boiling point of 100° C. or higher and 150° C. or lower, and a hydrocarbon series solvent such as heptane and an aromatic series solvent such as toluene are preferred. The reaction was performed under nitrogen gas flow at a temperature of 120 to 260° C. for 5 to 20 hours, and excessive carboxylic acids are removed under reduced pressure at the time point that the hydroxyl value reaches 3.0 mgKOH/g or lower, for example. Thereafter, the carboxylic acids are removed with an alkali and operations including steaming and adsorption treatment using activated clay, acid clay or a synthetic adsorbent are performed alone or in combination to obtain the ester for the refrigerator oil.

According to the present invention, two or more kinds of the esters for the refrigerator oil synthesized by the methods described above may be mixed and used.

To the ester for the refrigerator oil of the present invention, it may be appropriately added additives, depending on the objects, including known additives such as phenolic oxidation prevention agents, metal inactivating agents including benzotriazole, thiadiazole or ditiocarbamate, acid scavengers including epoxy compounds or carbodiimide, phosphorus-based extreme pressure compounds, or the like.

EXAMPLES

The present will be described further in detail below.
(Method of Synthesis)
"D-PE" and "T-PE" supplied by KOEI CHEMNICAL Co. LTD., were used as dipentaerythritol and tripentaerythritol. N-pentanoic acid and 2-methyl butanoic acid were synthesized using agents supplied by TOKYO CHEMICAL INDUSTRY CO. LTD.

A thermometer, nitrogen-supplying tube, agitator, Dimroth condenser and oil-water separation tube of a volume of 30 ml were equipped to a four-necked flask of 2 liter. 440 g (1.7 mol) of dipentaerythritol and 23 g (0.06 mol) of tripentaerythritol were charged in the flask. 700 g (6.85 mol) of n-pentanoic acid and 467 g (4.57 mol) of 2-methyl butanoic acid were then added so that the molar ratio of carboxylic acids with respect to hydroxyl group of the charged alcohols was made 1.05. It was finally charged 6.2 g (0.02 mol) or 0.2 mol equivalent of titanium isopropoxide with respect to the hydroxyl groups of the charged alcohols.

The charged reaction solution was heated under nitrogen gas flow at 220° C. until the hydroxyl value of the ester reached 3 or lower. Thereafter, the inside of the reactor was cooled to 200° C. and the pressure was lowered to 80 Torr, so that excessive fatty acids were evaporated until the acid value reached 5 mgKOH/g or lower.

After the reactor was cooled to 85° C., 1.5 equivalent of amount of potassium hydroxide calculated from the acid value was diluted with ion exchange water to produce 10 percent aqueous solution, which was added to the reaction solution, followed by agitation for 1 hour. After the agitation was terminated, it was stood still for 30 minutes so that aqueous layer separated as the lower layer was removed. Then, 20 mass percent of ion exchange water was added to the reaction solution, which was agitated at 85° C. for 10 minutes and stood still for 15 minute to separate the aqueous layer, which was then removed. The operations were repeated until pH of the aqueous layer reached 7 to 8. Thereafter, it was agitated at 100° C. and 30 Torr for 1 hour to remove water. 2 mass percent of active clay was finally added to the reaction solution, which was then stirred under condition of 80° C. and 30 Torr for 1 hour and filtrated to remove the adsorbent, so that the desired ester for the refrigerator oil was obtained.

(Method of Analyzing Composition)

10 ml of 0.5N KOH ethanol solution was added to the thus obtained ester for the refrigerator oil, which was subjected to decomposition by saponification at 80° C. for 8 hours. Excessive amount of hydrochloric acid was added to the thus obtained sample for the neutralization and 40 ml of hexane and 20 ml of ion exchange water were added, followed by agitation, standing and layer separation.

Hexane was evaporated from hexane layer, to which 2 ml of methanol solution of boron trifluoride was added. The layer was then heated at 60° C. for 30 minutes to perform the methyl esterification and the quantity of mono carboxylic acids was determined by gas chromatography.

Ion exchange water was evaporated at a reduced pressure from aqueous layer, which was then dried by storing in a temperature constant bath at 105° C. for 1 hour. 10 ml of isopropyl alcohol was then used to extract alcohol. Isopropyl alcohol was evaporated and it was performed the trimethylsilylation according to a conventional method. The quantity of the alcohol was determined by gas chromatography.

Color phase: It was measured based on JOCS 2.2.1.4-1996

Acid value: It was measured based on JIS K-0070.

Total acid value: It was measured based on JIS C-2101.

Hydroxyl value: It was measured based on JIS K-0070.

The operations described above were performed and the ratio of the alcohols and carboxylic acids was changed to synthesize esters for refrigerator oils. The thus obtained esters for the refrigerator oils were subjected to analysis of composition. Table 1 summarizes the results of the analysis of the composition, R-value as described above, and color phase, acid value and hydroxyl value of the ester for the refrigerator oil.

TABLE 1

| | Mixed alcohols (G C %) | | Mixed monocarboxylic Acids (G C %) | | | Color phase (APHA) | Total acid value (mgKOH/g) | Hydroxyl value (mgKOH/g) |
|---|---|---|---|---|---|---|---|---|
| | diPE | triPE | nC5 | iC5 | R | | | |
| Ex. 1 | 95 | 5 | 58 | 42 | 14 | 30 | 0.01 or lower | 0.5 |
| Ex. 2 | 99.7 | 0.3 | 64 | 36 | 160 | 30 | 0.01 or lower | 0.4 |
| Ex. 3 | 91 | 9 | 69 | 31 | 5 | 40 | 0.01 or lower | 0.3 |
| Ex. 4 | 92 | 8 | 64 | 36 | 6 | 40 | 0.01 or lower | 0.4 |
| Ex. 5 | 99 | 1 | 78 | 22 | 51 | 30 | 0.01 or lower | 0.3 |
| Ex. 6 | 93 | 7 | 53 | 47 | 11 | 40 | 0.01 or lower | 0.8 |
| Ex. 7 | 98 | 2 | 68 | 32 | 20 | 30 | 0.01 or lower | 0.3 |
| Com. Ex. 1 | 99.9 | 0.1 | 57 | 43 | 754 | 30 | 0.01 or lower | 0.5 |
| Com. Ex. 2 | 84 | 16 | 58 | 42 | 4 | 50 | 0.01 or lower | 0.5 |
| Com. Ex. 3 | 94 | 6 | 28 | 72 | 40 | 50 | 0.01 or lower | 0.9 |
| Com. Ex. 4 | 95 | 5 | 87 | 13 | 3 | 30 | 0.01 or lower | 0.1 |

(※) diPE: Dipentaerythritol
triPE: Tripentaerythritol
nC5: n-pentanoic acid
iC5: 2-methyl butanoic acid Each ester for the refrigerator oil was evaluated according to the following methods.
(Kinematic Viscosity)
It was measured based on JIS K-2283.
(Two-Layer Separation Temperature)
The two-layer separation temperature at a low temperature region was measured based on JIS K-2211 and under the condition that the mass ratio of R-32 refrigerant and the ester for the refrigerator oil was 8:2. The thus obtained separation temperatures were evaluated based on the following standard.
⊚: It is not higher than minus 35° C.
○: It is higher than minus 35° C. and not higher than minus 30° C.
Δ: It is higher than minus 30° C. and not higher than minus 20° C.
x: it is higher than minus 20° C.
(Heat Resistance Test: Shield Tube Test)
2 g of the ester for the refrigerator oil whose water content was adjusted at about 1000 ppm in advance, 3 g of the refrigerant R-32, and each one of metal pieces of iron, copper and aluminum having a length of 10 mm were enclosed and sealed in a thick Pyrex (Registered trade name) tube (total length of 300 mm, outer diameter of 10 mm and inner diameter of 6 mm). This was heated at 200° C. for 10 days and opened to draw the refrigerant. The resultant acid value was measured based on JIS C-2101. The resultant acid value was evaluated based on the following standard.
⊚: It is not higher than 0.05 mgKOH/g.
○: It is higher than 0.05 mgKOH/g and not higher than 0.1 mgKOH/g.
Δ: It is higher than 0.1 mgKOH/g and not higher than 0.15 mgKOH/g.
x: It is higher than 0.15 mgKOH/g.
(Lubrication Test)
Falex Test Pin Wear Amount:
Falex pin wear test was performed based on ASTM D-2670, while R-32 refrigerant was blown into the ester for the refrigerator oil at a rate of 150 ml/min. The temperature of a sample was made 100° C., and running-in operation was performed for 1 minute at a load of 150 pounds, followed by running for 1 hour at a load of 300 pound. The wear amount of the pin after the completion of the operation was measured. The thus obtained wear amount of the pin was evaluated based on the following standard.
⊚: It is not higher than 8.0 mg.
○: It is higher than 8.0 mg and not higher than 10.0 mg.
Δ: It is higher than 10 mg and not higher than 13.0 mg.
x: It is higher than 13.0 mg.
The results of the evaluation were summarized in table 2.

TABLE 2

| | Kinematic viscosity at 40° C. (mm²/s) | Two-layer separation temperature | | Heat resistance test | | Test of lubrication property | |
|---|---|---|---|---|---|---|---|
| | | R-32, low temperature, (° C.) | Evaluation | Acid value (mgKOH/g) | Evaluation | (pin wear amount, mg) | Evaluation |
| Ex. 1 | 74 | −37 | ⊚ | 0.05 | ⊚ | 7.1 | ⊚ |
| Ex. 2 | 57 | −36 | ⊚ | 0.03 | ⊚ | 9.3 | ○ |
| Ex. 3 | 79 | −33 | ○ | 0.08 | ○ | 5.0 | ⊚ |
| Ex. 4 | 79 | −33 | ○ | 0.03 | ⊚ | 6.0 | ⊚ |
| Ex. 5 | 52 | −33 | ○ | 0.05 | ⊚ | 9.3 | ○ |
| Ex. 6 | 90 | −40 | ⊚ | 0.08 | ○ | 7.0 | ⊚ |
| Ex. 7 | 60 | −35 | ⊚ | 0.04 | ⊚ | 7.0 | ⊚ |
| Com. Ex. 1 | 59 | −38 | ⊚ | 0.03 | ⊚ | 14.2 | X |
| Com. Ex. 2 | 105 | −35 | ⊚ | 0.13 | Δ | 5.0 | ⊚ |
| Com. Ex. 3 | 98 | −46 | ⊚ | 0.04 | ⊚ | 13.8 | X |
| Com. Ex. 4 | 56 | −28 | Δ | 0.13 | Δ | 4.0 | ⊚ |

As shown in the examples 1 to 7, according to the present invention, it can be obtained the ester for the refrigerator oil excellent in compatibility with R-32 refrigerant and heat resistant and lubrication properties.

According to the comparative example 1, as the ratio of dipentaerythritol is high, the lubrication property is deteriorated.

According to the comparative example 2, as the ratio of dipentaerythritol is low, the heat resistant property is deteriorated.

According to the comparative example 3, as the ratio of n-pentanoic acid is low, the lubrication property is deteriorated.

According the comparative example 4, as the ratio of n-pentanoic acid is high, the heat resistant property is deteriorated and the two-layer separation temperature is high on the low temperature side.

The invention claimed is:

1. An ester for a refrigerator oil and of mixed alcohols and mixed monocarboxylic acids,
   wherein said mixed alcohols consist of dipentaerythritol and tripentaerythritol in a mass ratio of 90/10 to 99.7/0.3;
   wherein said mixed monocarboxylic acids consist of n-pentanoic acid and 2-methyl butanoic acid in a mass ratio of 50/50 to 80/20; and
   wherein said ester has a kinematic viscosity of 50 to 150 mm$^2$/s at 40° C.

2. A working fluid composition for a refrigerator, said fluid composition comprising said ester for said refrigerator oil of claim 1 and R-32 refrigerant.

* * * * *